United States Patent [19]
Kehr et al.

[11] 3,931,287
[45] Jan. 6, 1976

[54] POLYENE COMPOUNDS

[75] Inventors: Clifton L. Kehr, Silver Spring; Walter R. Wszolek, Sykesville, both of Md.

[73] Assignee: W. R. Grace & Co., New York, N.Y.

[22] Filed: Aug. 22, 1973

[21] Appl. No.: 390,665

Related U.S. Application Data

[63] Continuation of Ser. No. 40,737, May 26, 1970, abandoned, which is a continuation-in-part of Ser. No. 617,801, Feb. 23, 1967, abandoned, which is a continuation-in-part of Ser. No. 567,841, July 26, 1966, abandoned.

[52] U.S. Cl. 260/471 C; 260/77.5 AN; 260/295 CA; 260/332.2 R; 260/347.4; 260/455 A; 260/468 E; 260/482 B
[51] Int. Cl.$^2$ .................................. C07C 125/06
[58] Field of Search.......... 260/471 C, 482 B, 468 E

[56] References Cited
UNITED STATES PATENTS 3,783,152   1/1974   Larsen ........................... 260/471 C

*Primary Examiner*—James A. Patten
*Assistant Examiner*—L. A. Thaxton
*Attorney, Agent, or Firm*—Eugene M. Bond

[57] ABSTRACT

The invention disclosed is for a new and novel class of liquid polyene compositions formed of a molecule containing at least two unsaturated carbon-to-carbon bonds disposed at terminal positions on a main chain backbone of the molecule. The molecule includes unsaturated carbon-to-carbon bonds connected by a divalent chemically compatible derivative to a stable, organic, polyvalent, and polymeric member free of reactive carbon-to-carbon unsaturation and free of highly water-sensitive members. The new class of liquid polyene compositions which have a molecular weight in the range 300 to 20,000, and a viscosity in the range from essentially 0 to 20 million centipoises at 70°C., may usefully form a component of a system which upon curing in the presence of a free radical generator and a polythiol, forms odorless, solid, elastomeric products. The cured products may be used as sealants, coatings, adhesives and molded articles.

5 Claims, No Drawings

POLYENE COMPOUNDS

The present application for U.S. Letters Patent is a continuation of copending application Ser. No. 40.737 filed May 26, 1970, now abandoned, which in turn is a continuation-in-part of application Ser. No. 617,801, filed Feb. 23, 1967, now abandoned, which in turn is a continuation-in-part of application Ser. No. 567,841, filed July 26, 1966, now also abandoned.

This invention relates to a new and novel class of liquid polyene compositions formed of a molecule containing at least two unsaturated carbon-to-carbon bonds disposed at terminal positions on a main chain backbone of the molecule. The molecule includes unsaturated carbon-to-carbon bonds connected by a divalent chemically compatible derivative to a stable, organic, polyvalent, and polymeric member free of reactive carbon-to-carbon unsaturation, and free of highly water-sensitive members. The new class of liquid polyene compositions have a molecular weight in the range 300 to 20,000, and a viscosity in the range from essentially 0 to 20 million centipoises at 70°C.

It is well known in the art that cure of internally unsaturated polymers such as polybutadiene or polyisoprene may be effected with polythiols. However, such polymers, due mainly to residual internal unsaturation after curing, are unstable either to thermal oxidation or ultra-violet catalyzed oxidation, and are subject to rapid attack by ozone. Eventually degradation and embrittlement results in the internal double bond polymers, substantially reducing their useful service life.

A limitation of commercially available liquid polyurethane prepolymers is the fact that they are terminated by isocyanate (—NCO) groups. These —NCO groups are extremely unstable in storage, and are highly water-sensitive such that under practical conditions, they react with traces of moisture from the atmosphere to form gaseous carbon dioxide and amino groupings which in turn react with more —NCO to form eventually a highly viscous, sometimes completely insoluble urea-extended chain network. In cases where insolubilization occurs, the polymer has to be discarded at great expense. Further, if the —NCO-terminated prepolymers come in contact with traces of either acidic or basic impurities, dimerization and/or trimerization of the —NCO functions may take place to form viscous, sometimes insoluble products during storage. Even mild alkalis such as those constituents normally present on the surface of glass vessels and containers may cause storage problems.

A further limitation for some applications is found in polyurethane polymers of the prior art which are derived from aromatic diisocyanates or polyisocyanates such as tolylene-2,4-diisocyanate, tolylene-2,6-diisocyanate, 4,4'-diisocyanatodiphenylmethane, and the like. These aromatic diisocyanates (or mixtures thereof) enjoy widespread use in polyurethane elastomers, foams, and coatings, because of their ready commercial availability, high degree of reactivity and relatively low cost. The derived polyurethane products, however, are known to turn yellow, amber, orange or brown in color when exposed to sunlight, ultraviolet light or other forms of actinic radiation. This yellowing tendency imparts a definite limitation on the usage of such polyurethanes in many applications. There is evidence in the technical literature that shows that this yellowing or discoloration problem is directly attributable to the aromatic (benzeneoid) nucleus in the aromatic diisocyanates, and accordingly serious yellowing problems in polyurethanes may be avoided by use of aliphatic polyisocyanates such as hexamethylene diisocyanate.

It has now been found that numerous defects of the prior art may be effectively overcome by practice of the present invention which provides a new and novel class of liquid polyenes which are curable by polythiols to solid polythioether resins or elastomers. When the polyenes of the present invention are compounded with polythiols, the prepared system may be stored safely for long periods of time in the absence of a free radical generator. Upon exposure to a free radical generator such as actinic light, the prepared system may be cured rapidly and controllably to polythioether-polyurethane product which is low in cost and equal or better in reaction rate in polymer formation when compared with prior art compositions.

Generally stated; the new class of polyenes of the present invention include a composition which comprises the formula:

[A]$_m$ wherein $m$ is an integer of at least 2; wherein X is a member selected from the group consisting of:

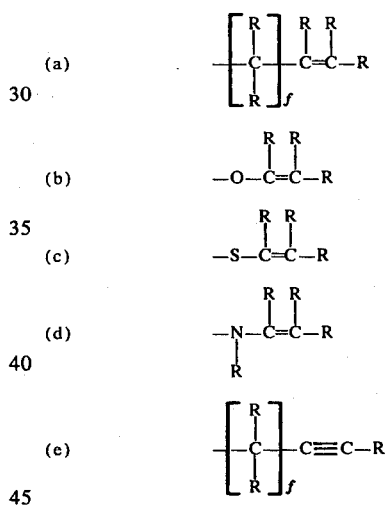

In the members (a) to (e), R is a radical selected from the group consisting of hydrogen, fluorine, chlorine, furyl, thienyl, pyridyl, phenyl, benzyl, alkyl, cycloalkyl, alkoxy, substituted phenyl, substituted benzyl, substituted alkyl, substituted cycloalkyl, and substituted alkoxy, the alkyl and alkoxy having from 1 to 9 carbon atoms, the cycloalkyl having from 3 to 8 carbon atoms, and the substituents on the substituted members are selected from the group consisting of nitro, chloro, fluoro, acetoxy, acetamido, phenyl, benzyl, alkyl and alkoxy of 1 to 9 carbon atoms, and cycloalkyl of 3 to 8 carbon atoms.

The members (a) to (e) are connected to [A] through a divalent chemically compatible derivative member of the group consisting of Si(R)$_2$, carboxylate, sulfone, urethane and substituted urethane, urea and substituted urea, amide and substituted amide, amine and substituted amine, alkyl and substituted alkyl, aryl and substituted aryl, cycloalkyl and substituted cycloalkyl. The alkyl members have from 1 to 9 carbon atoms, the aryl members are either phenyl or naphthyl, and the cycloalkyl members have from 3 to 8 carbon atoms with R and said members substituted being defined above.

The member [A] is stable, organic, polyvalent, and polymeric; free of reactive carbon-to-carbon unsaturation; free of highly water-sensitive members; and consisting of atoms disposed in main chain series and selected from the group consisting of carbon, oxygen, nitrogen, phosphorus, and silicon. The main chain series is formed of at least two repeating units selected from the group consisting of $-(CH_2)_g$, $-(C_2H_4O)_h$, $-(C_3H_6O)_h$, and $-(C_4H_8O)_h$ and having pendant substituent atoms of the group consisting of carbon, hydrogen, chlorine, bromine, oxygen and nitrogen. The symbol $g$ is an integer from 1 to 9, and the symbol $h$ is an integer from 1 to 200.

The composition has a molecular weight in the range 300 to 20,000, and a viscosity in the range from essentially 0 to 20 million centipoises at 70°C. as measured by a Brookfield Viscometer. More particularly, the member [A] of the polyene composition may be formed primarily of alkyl radicals, phenyl and urethane derivatives, oxygenated radicals, and nitrogen substituted radicals. The member [A] may also be represented by the formula:

$$R_2 - \left( -CH_2 - \underset{R_3}{\underset{|}{\overset{H}{\overset{|}{C}}}} - \right)_j \left( -CH_2 - \underset{R_4}{\underset{|}{\overset{H}{\overset{|}{C}}}} - \right)_k R_2$$

wherein
  $j$ and $k$ are integers greater than 1;
  $R_2$ is a member of the group consisting of hydrogen, and alkyl having 1 to 9 carbon atoms;
  $R_3$ is a member of the group consisting of hydrogen, and saturated alkyl having 1 to 9 carbon atoms;
  $R_4$ is a divalent derivative of the group consisting of phenyl, benzyl, alkyl, cycloalkyl, substituted phenyl, substituted benzyl, substituted alkyl and substituted cycloalkyl; with the terms alkyl, cycloalkyl and members substituted being defined above.

General representative formulas for the polyenes of the present invention may be prepared as exemplified below:

I — Poly (alkylene-ether) Polyol Reacted with Unsaturated Monoisocyanates Forming Polyurethane Polyenes and Related Polymers Interconnected-Modified Difunctional Interconnected-Modified Tetrafunctional II — Poly (alkylene-ester) Polyol Reacted with Unsaturated Monoissocyanates Forming Polyurethane Polyenes and Related Polymers Difunctional

Interconnected-Modified Difunctional

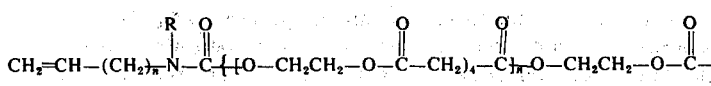

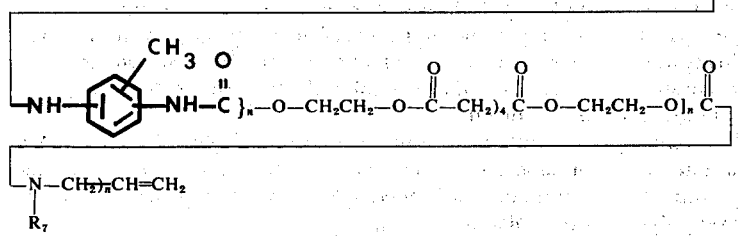

III — Poly (alkylene-ether) Polyol Reacted With Polyisocyanate and Unsaturated Monoalcohol Forming Polyurethane Polyenes and Related Polymers

Difunctional

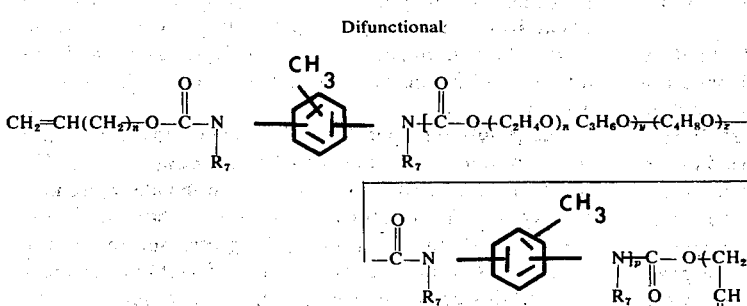

Trifunctional

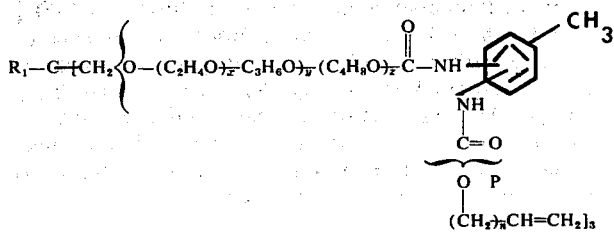

Tetrafunctional

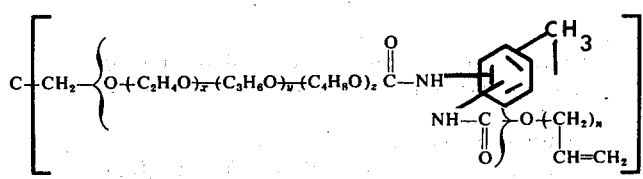

In the above formulas, the sum of $x + y + z$ in each chain segment is at least 1; P is an integer of 2 or more; $q$ is at least 2; $n$ is at least 1; $R_1$ is selected from the group consisting of hydrogen, phenyl, benzyl, alkyl, cycloalkyl, and substituted phenyl; and $R_7$ is a member of the group consisting of $CH_2=CH+CH_2)_{\overline{n}}$, hydrogen, phenyl, cycloalkyl, and alkyl.

A general method of forming one type of polyene containing urethane groups is to react a polyol of the general formula $R_{11}+OH)_n$ wherein $R_{11}$ is a polyvalent organic moiety free from reactive carbon-to-carbon unsaturation and $n$ is at least 2; with a polyisocyanate of the general formula $R_{12}+NCO)_n$ wherein $R_{12}$ is a polyvalent organic moiety free from reactive carbon-to-carbon unsaturation and $n$ is at least 2 and a member of the group consisting of an ene-ol, yne-ol, ene-amine and yne-amine. The reaction is carried out in an inert moisture-free atmosphere (nitrogen blanket) at atmospheric pressure at a temperature in the range from 0° to about 120° C for a period of about 5 minutes to about 25 hours. In the case where an ene-ol or yne-ol is employed, the reaction is preferably a one step reaction wherein all the reactants are charged together. In the case where an ene-amine or yne-amine is used, the reaction is preferably a two step reaction wherein the polyol and the polyisocyanate are reacted together and thereafter preferably at room temperature, the ene-amine or yne-amine is added to the NCO terminated polymer formed. The group consisting of ene-ol, yne-ol, ene-amine and yne-amine are usually added to the reaction in an amount such that there is one carbon-to-carbon unsaturation in the group member per hydroxyl group in the polyol and said polyol and group member are added in combination in a stoichiometric amount necessary to react with the isocyanate groups in the polyisocyanate.

A second general method of forming a polyene containing urethane groups (or urea groups) is to react a polyol (or polyamine) with an ene-isocyanate or an yne-isocyanate to form the corresponding polyene. The general procedure and stoichiometry of this synthesis route is similar to that described for polyisocyanates in the preceding. In this instance, a polyol reacts with an ene-isocyanate to form the corresponding polyene. It is found, however, that products derived from this route, when cured in the presence of a free radical generator and a polythiol, form relatively weak solid polythioether products. To obtain practical cured products having commercially useful physical strength characteristics, it is desirable to provide polar functional groupings within the main chain backbone of the polymeric polyene. These polar functional groupings serve as connecting linkages between multiple repeating units in the main chain series, and serve as internal strength-reinforcing agents by virtue of their ability to create strong interchain attraction forces between molecules of polymer in the final cured composition.

Polyenes containing ester groups may be formed by reacting an acid of the formula $R_{13}$—$(COOH)_n$ wherein $R_{13}$ is a polyvalent organic moiety free from reactive carbon-to-carbon unsaturation and $n$ is at least 2; with either an ene-ol or yne-ol. The reaction is carried out in an inert moisture-free atmosphere (nitrogen blanket) at atmospheric pressure at a temperature in the range from 0° to about 120°C. for a period of 5 minutes to 25 hours. Usually the reaction is carried out in the presence of a catalyst (p-toluene sulfonic acid) and in the presence of a solvent, e.g. xylene at refluxing temperature. The water formed is azeotroped off of the reaction.

Another method of making an ester containing polyene is to react a polyol of the formula $R_{11}$—$(OH)_n$ wherein $R_{11}$ is a polyvalent organic moiety free from reactive carbonto-carbon unsaturation and $n$ is at least 2; with either an ene-acid or an yne-acid. The reaction is carried out in the same manner as set out above for the ester-containing polyenes. In practicing this latter technique, however, it may be found that ene-acids (or yne-acids) in which the ene (or yne) group is adjacent to an activating polar moiety such as

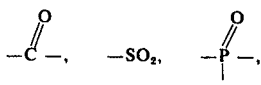

and the like are generally not desirable within the scope of this invention. These activated ene compounds are very prone to self-polymerization reactions to form vinyl polymers. Excessive amounts of self-polymerization of the ene groups is an undesirable side reaction in the present invention since the desired polythioether reaction products are precluded whenever self-polymerization of the ene groups occurs. Finally, the presence of activated, easily self-polymerizable ene groups in the composition leads to oxygen inhibition during curing, storage stability problems, or the need for excessively high inhibitor concentrations.

In forming the urethane-containing polyenes of the present invention, catalytic amounts of a catalyst may be employed to speed up the reaction. This is especially true in the case where an ene-ol is used to form the polyene. Such catalysts are well known to those in the art and include organometallic compounds such as stannous octoate, stannous oleate, dibutyl tin dilaurate, cobalt acetylacetonate, ferric acetylacetonate, lead naphthanate and dibutyl tin diacetate.

In summary, by admixing polyenes or polyynes containing two or more reactive unsaturated carbon-to-carbon bonds located terminal from the main chain with a polythiol containing two or more thiol groups per molecule and thereafter exposing said liquid mixture to free-radical generators, there is provided an essentially odorless solid elastomeric or resinous polymeric product.

Polythiol as used herein refers to simple or complex organic compounds having a multiplicity of pendant or terminally positioned —SH functional groups per average molecule.

On the average the polythiol must contain 2 or more —SH groups/molecule and have a viscosity range of essentially 0 to 20 million centipoises (cps) at 70°C as measured by a Brookfield Viscometer when in the presence of an inert solvent, aqueous dispersion or plasticizer. Operable polythiols in the instant invention usually have molecular weights in the range about 50 to about 20,000, and preferably from about 100 to about 10,000.

The polythiols operable in the instant invention may be exemplified by the general formula $R_8$—$(SH)_n$ where $n$ is at least 2 and $R_8$ is a polyvalent organic moiety free from reactive carbon-to-carbon unsaturation. Thus $R_8$ may contain cyclic groupings and minor amounts of hetero atoms such as N, P or O but primarily contains carbon-carbon, carbon-hydrogen, carbon-oxygen, or silicon-oxygen containing chain linkages free of any reactive carbon-to-carbon unsaturation.

One class of polythiols operable with polyenes to obtain essentially odorless polythioether products are esters of thiol-containing acids of the formula HS-$R_6$-COOH where $R_9$ is an organic moiety containing no reactive carbon-to-carbon unsaturation with polyhydroxy compounds of structure $R_{10}$—$(OH)_n$ where $R_{10}$ is an organic moiety containing no reactive carbon-to-carbon unsaturation, and $n$ is 2 or greater. These components will react under suitable conditions to give a polythiol having the general structure:

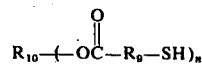

where $R_9$ and $R_{10}$ are organic moieties containing no reactive carbon-to-carbon unsaturation, and $n$ is 2 or greater.

Certain polythiols such as the aliphatic monomeric polythiols (ethane dithiol, hexamethylene dithiol, decamethylene dithiol, tolylene-2,4-dithiol, and the like, and some polymeric polythiols such as a thiol-terminated ethylcyclohexyl dimercaptan polymer, and the like, and similar polythiols which are conveniently and ordinarily synthesized on a commercial basis, although having obnoxious odors, are operable but many of the end products are not widely accepted from a practical, commercial point of view. Examples of the polythiol compounds preferred because of relatively low odor level include but are not limited to esters of thiogylcolic acid (HS—$CH_2$COOH), α-mercaptopropionic acid (HS—CH($CH_3$)—COOH and β-mercaptopropionic acid (HS—$CH_2CH_2$COCH) with polyhydroxy compounds such as glycols, triols, tetraols, pentaols, hexaols, and the like. Specific examples of the preferred polythiols include but are not limited to ethylene glycol bis (thioglycolate), ethylene glycol bis (β-mercaptopropionate), trimethylolpropane tris (thioglycolate), trimethylolpropane tris (β-mercaptopropionate), pentaerythritol tetrakis (thioglycolate) and pentaerythritol tetrakis (β-mercaptoproprionate), all of which are commercially available. A specific example of a preferred polymeric polythiol is polypropylene ether glycol bis (β-mercaptopropionate) which is prepared from polypropylene-ether glycol (e.g. Pluracol P2010, Wyandotte Chemical Corp.) and β-mercaptopropionic acid by esterification.

The preferred polythiol compounds are characterized by a low level of mercaptan-like odor initially, and after reaction, give essentially odorless polythioether end products which are commercially attractive and practically useful resins or elastomers for both indoor and outdoor applications.

Prior to curing, the curable liquid polymer may be formulated for use as 100% solids, or disposed in organic solvents, or as dispersions or emulsions in aqueous media.

To obtain the maximum strength, solvent resistance, creep resistance, heat resistance and freedom from tackiness, the reaction components consisting of the polyenes and polythiols are formulated in such a manner as to give solid, crosslinked, three dimensional network polythioether polymer systems on curing. In order to achieve such infinite network formation the individual polyenes and polythiols must have a functionality of at least 2 and the sum of the functionalities of the polyene and polythiol components must always be greater than 4. Blends and mixtures of the polyenes and the polythiols containing said functionality are also operable herein.

The compositions to be cured may, if desired, include such additives as antioxidants, accelerators, dyes, inhibitors, activators, fillers, pigments, anti-static agents, flame-retardant agents, thickeners, thixotropic agents, surface-active agents, viscosity modifiers, extending oils, plasticizers, tackifiers and the like. Such additives are usually preblended with the polyene or polythiol prior to or during the compounding step. The additives may be present in quantities up to 500 parts or more per 100 parts polyene or polythiol by weight and preferably from 0.005 to about 300 parts on the same basis.

The curable liquid polymer compositions prior to curing may readily be pumped, poured, siphoned, brushed, sprayed, doctored, or otherwise handled as desired. Following application, curing in place to a solid resin or elastomer may be effected either very rapidly or extremely slowly as desired by manipulation of the compounding ingredients and the method of curing.

The liquid polythioether-forming components and compositions, prior to curing, may be admixed with or blended with other monomeric and polymeric materials such as thermoplastic resins, elastomers or thermosetting resin monomeric or polymeric compositions. The resulting blend may be subjected to conditions for curing or co-curing of the various components of the blend to give cured products having unusual physical properties.

The curing reaction may be initiated by any free radical mechanism which dissociates or abstracts a hydrogen atom from an SH group, or accomplishes the equivalent thereof. Thus it is possible merely to expose the polyene and polythiol admixture to ambient conditions (oxygen from the air is the initiator) and obtain a cured solid elastomeric or resinous product. Azo compounds or peroxides (with or without amine accelerators) which decompose at ambient conditions are also operable as free radical generating agents capable of curing the components of the instant invention to solid odorless elastomeric or resinous polymer products. Additionally, ultraviolet light (with or without curing rate accelerators such as chemical photoinitiators, or sensitizers such as benzophenone, acetophenone, acenaphthlene-quinone) or other forms of energetic radiation yield rapid cures.

It is also possible, if desired, to use various forms of high energy irradiation for curing. Peroxides and hydroperoxides, whether or not accelerated, presently used in the curing of unsaturated polyesters are operable as free radical generators to initiate curing. Examples of some operable peroxides and accelerators include but are not limited to, benzoyl peroxide with dimethylaniline as an accelerator, cumene hydroperoxide with cobalt naphthenate as an accelerator and cyclohexanone peroxide with either of the aforementioned accelerators. The peroxides and hyroperoxides may also be generated in situ if so desired.

The curing period may be retarded or accelerated from less than 1 minute to 30 days or more. Conventional curing initiators or accelerators operable include, but are not limited to oxygen; peroxides, hydroperoxides, peracids; persulfates, azo compounds such as azobis-isovaleronitrile; ultraviolet light (with or without coagent sensitizers); high energy radiation such as x-rays, β-rays, electron beams, gamma radiation, and the like; ozone; oxidizing agents such as $PbO_2$; and cyclohexanone peroxide with dimethyl aniline. Conventional curing inhibitors or retarders include but are not limited to hydroquinone; p-tert-butyl catechol; 2,6-ditert-butyl-p-methylphenol; phenothiazine; N-phenyl-2-napthylamine; inert gas atmospheres such as helium, argon, nitrogen, and carbon dioxide; vacuum; and the like.

The following examples are given to further illustrate the present invention. In all cases, unless otherwise noted, all parts and percentages are by weight.

FORMATION OF POLYENE PREPOLYMER

Example 1

458 g. (0.23 moles) of a commercially available liquid polymeric diisocyanate sold under the tradename "Adiprene L-100" by E. I. duPont de Nemours & Co. was charged to a dry resin kettle maintained under a nitrogen atmosphere and equipped with a condenser, stirrer, thermometer, and gas inlet and outlet. 37.8 g. (0.65 moles) of allyl alcohol was charged to the kettle and the reaction was continued for 17 hours with stirring at 100°C. Thereafter the nitrogen atmosphere was removed and the kettle was evacuated 8 hours at 100°C. 50 cc. dry benzene was added to the kettle and the reaction product was azeotroped with benzene to remove the unreacted alcohol. This allyl terminated liquid prepolymer had a molecular weight of approximately 2,100 and will be referred to as Prepolymer A hereinafter.

Example 2

400 g. (0.2 moles) of "Adiprene L-100" was charged to a dry resin kettle maintained under nitrogen and equipped with a condenser, stirrer, thermometer and gas inlet and outlet. 25.2 g. (0.43 moles) of propargyl alcohol (HC ≡ C—CH₂OH) was added to the kettle and the reaction was continued with stirring for 18 hours at 160°C. Thereafter the nitrogen atmosphere was removed and the kettle was evacuated 16 hours at 100°C followed by azeotropic distillations with 50 cc. water and then 50 cc. benzene to remove any excess propargyl alcohol. This HO ≡ C— terminated liquid prepolymer had a viscosity of 27,500 centiposes at 70°C. and a molecular weight of 2100 and will be referred to as Prepolymer B hereinafter.

Example 3

1 mole of commercially available poly(ethylene ether) glycol having a molecular weight of 1450 and a specific gravity of 1.21 was charged to a resin kettle maintained under nitrogen and equipped with a condenser, stirrer, thermometer and a gas inlet and outlet. 2.9 g. dibutyl tin dilaurate as a catalyst was charged to the kettle along with 2 moles of an 80/20 mixed isomer blend of tolylene-2,4-diisocyanate/tolylene-2,6-diisocyanate and 2 moles of allyl alcohol. The reaction was continued with stirring at 60°C for 2 hours. Thereafter a vacuum of 1 mm. was applied for 2 hours at 60°C to remove the excess alcohol. This CH₂=CH— terminated prepolymer had a molecular weight of approximately 1,950 and will hereinafter be referred to as Prepolymer C.

Example 4

1 mole of a commercially available poly (propylene ether) glycol having a molecular weight of about 1958 and a hydroxyl number of 57.6 was charged to a resin kettle equipped with a condenser, stirrer, thermometer and a gas inlet and outlet. 4 g. of dibutyl tin dilaurate as a catalyst was added to the kettle along with 348 g. (2.0 moles) of an 80/20 mixed isomer blend of tolylene-2,4-diisocyanate/tolylene-2,6-diisocyanate and 116 g. (2 moles) of allyl alcohol. The reaction was carried out for 20 minutes at room temperature under nitrogen. Excess alcohol was stripped from the reaction kettle by vacuum over a 1 hour period. The thus formed CH₂=CH— terminated liquid prepolymer had a molecular weight of approximately 2,400 and will hereinafter be referred to as Prepolymer D.

Example 5

750 g. of a N-containing tetrol (hydroxyl functionality equal to 4) available from Wyandotte Chemicals Corp. under the tradename "Tetronic Polyol 904" having a M.W. of 7,500 was placed in a reaction vessel heated at 110°C. The flask was maintained under vacuum for 1 hour. Then, under an atmosphere of nitrogen, 0.1 cc. dibutyl tin dilaurate was added and the flask was cooled to 50°C. Now 18.3 g. allyl isocyanate was added slowly, maintaining the temperature at about 95°C for about 1 hour after the addition was completed. The thus formed polymeric polyene (i.e., Prepolymer E hereinafter) had a theoretical allyl functionality of 2.2, a theoretical hydroxyl functionality of 1.8, and a calculated molecular weight of about 7,683.

Example 6

To a resin kettle maintained under a nitrogen atmosphere and equipped with a condenser, stirrer, and thermometer and gas inlet and outlet was added 843 g. of a commercially available liquid diisocyanate prepolymer sold under the tradename "Multrathane F-196" by Mobay Chemical Co., said prepolymer having a molecular weight of about 1,680 and an available isocyanate content of 4.7 – 5.2%. 87 g. (1.5 moles) of allyl alcohol was added to the kettle and the reaction was continued for 18 hours at 140°C with stirring. Thereafter the nitrogen atmosphere was removed and the kettle was evacuated for 22 hours at 100°C. 50 cc. of dry benzene was added to the kettle and the reaction product was azeotroped therewith to remove any unreacted alcohol. This CH₂=CH— terminated liquid prepolymer had a viscosity of 25,000 centipoises at 70°C and a molecular weight of approximately 1800 and will be referred to as a Prepolymer F hereinafter.

Example 7

Following the procedure of Example 3, and using necessary reactants, a polyene of the following formula was prepared:

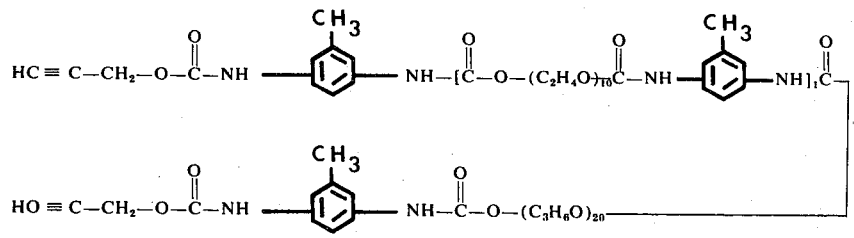

Example 8

A crotyl-terminated polyurethane which contains two reactive double bonds per average molecule in a near terminal position was prepared following the general procedure of Example 3. The resulting polymeric polyene was found to have the following formula:

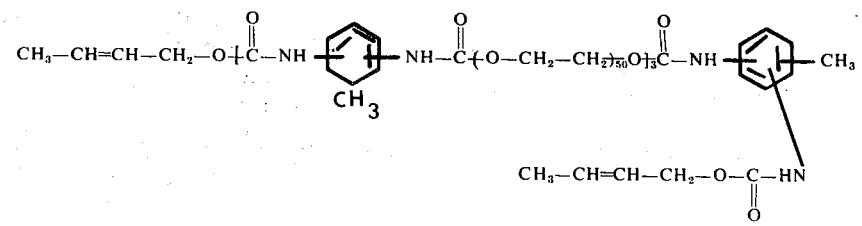

Example 9

Following the procedure of Example 3, and using necessary reactants, a polyene of the following formula was prepared:

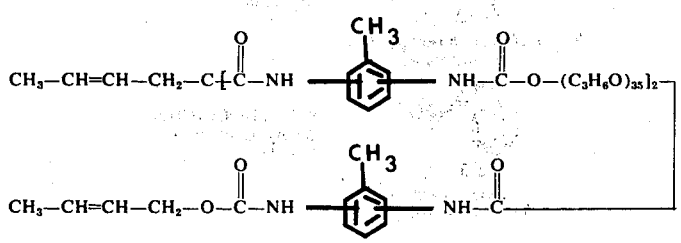

Example 10

Following the procedure of Example 3, and using necessary reactants, a polyene of the following formula was prepared:

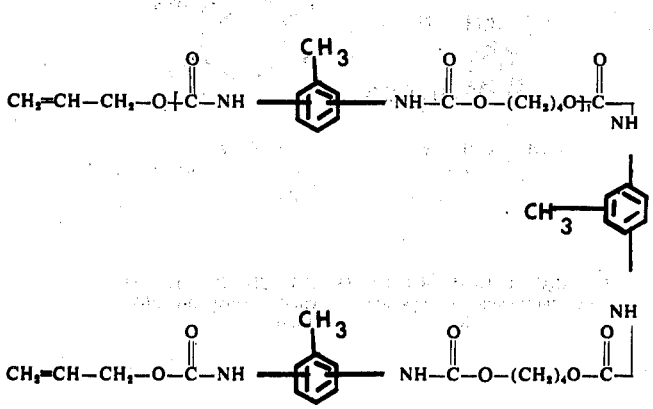

Example 11

To a liter 4 neck flask was charged 300 milliliters of dimethylformamide, 35 g. of an 80/20 mixed isomer blend of tolylene-2,4-diisocyanate/tolylene-2,6-diisocyanate and 0.1 cc. of dibutyl tin dilaurate. A mixture of 11.6 g. of allyl alcohol and 22.8 g. of hexol commercially available from Union Carbide Chemical Co. under the tradename "NIAX Polyol LS-490" having a molecular weight of 684 was slowly added to the flask. Temperature was kept at approximately 65°C during the addition and for a period of 1 hour. The polymeric product obtained had an average molecular weight of approximately 2,100.

Example 12

To a 1 liter 4 neck flask was charged 300 g. of a polyester diol (molecular weight 3232) sold under the tradename "RC Polyester S 101-35" by R. C. Division, Hooker Chemical Corp. and 0.1 cc. of dibutyl tin dilaurate. The flask was heated to 110°C of dibutyl tin dilaurate. The flask was heated to 110°C under vacuum and maintained thereat for 1 hour. The flask was cooled to approximately 60°C, nitrogen was admitted, and 7.7 g. allyl isocyanate and 8.1 g. of tolylene-2,4-diisocyanate was added by means of a dropping funnel to the reaction at a moderate rate. A maximum temperature of 90°C was needed. When the addition was complete the reaction was allowed to continue at 70°C for 1 hour. The thus formed solid polymeric product had an average molecular weight of approximately 6,800 and a viscosity of 13,600 centipoises when measured on a brookfield Viscometer at 70°C.

EXAMPLE 13

To a 1 liter 4 neck flask heated at 110°C was charged 808 g. of a polyester diol (having a molecular weight 3232) sold under the tradename "RC Polyester S 101-35" by R. C. Division, Hooker Chemical Corp. and 0.1 cc. dibutyl tin dilaurate. The flask was maintained under vacuum at 110°C for 1 hour. The flask was cooled to approximately 50°C and with nitrogen passing through, a mixture of 10 g. of allyl alcohol and 60 g. of an 80/20 mixed isomer blend of tolylene-2,4-diisocyanate/tolylene-2,6-diisocyanate was added via a dropping funnel at a moderate rate. The reaction was allowed to continue for 15 minutes. A maximum temperature of 90°C was produced by the exothermic reaction. The polymeric product obtained was a solid at room temperature but liquid at 70°C. The product had an average molecular weight of approximately 10,500 and a viscosity of 270,000 centipoises at 70° C.

Examples 14–23

Following the general procedure of the prior examples, and using the necessary reactants, a series of polyenes having the formula: $X + B - A)_{\overline{n}} B - X$ where $n$ is 2 or greater were prepared wherein the derivative members forming the polyenes are defined in the following:

| Example No. | Component [A] | Component [B] | Component [X] |
|---|---|---|---|
| 14. | HO—CH₂—C(CH₂Br)(CH₂Br)—CH₂—OH<br>Dibromoneopentyl glycol<br>DOW SA-1138<br>3 moles | 2,6-/2,4-tolylene diisocyanate blend - 4 moles | CH₂=C(Cl)—CH₂OH<br>2-Chloro-2-propanol-1<br>2 moles |
| 15. | HO—CH₂—C(CH₂Br)(CH₂Br)—CH₂OH<br>Dibromoneopentyl glycol<br>DOW SA-1138<br>5 moles | 2,6-/2,4-tolylene diisocyanate blend - 6 moles | CH₂=CHOCH₂CH₂OH<br>2-vinyloxyethanol<br>2 moles |
| 16. | HO—CH₂—C(CH₂Br)(CH₂Br)—CH₂OH<br>Dibromoneopentyl glycol<br>DOW SA-1138<br>40 moles | OCNCH₂CH₂CH₂CH₂CH₂CH₂NCO<br>hexamethylene diisocyanate<br>41 moles | CH≡C—CHOH(phenyl)<br>1-phenyl-2-propynol-1<br>2 moles |
| 17. | N,N,N¹,N¹-tetrakis(2-hydroxypropyl) ethylene diamine<br>Wyandotte, Quadrol<br>2 moles | 1,3-xylylene diisocyanate<br>7 moles | 1-methyl-2-methylolcyclohexene<br>6 moles |
| 18. | N,N,N¹,N¹-tetrakis (2-hydroxypropyl) ethylene diamine<br>Wyandotte Quadrol<br>2 moles | OCNCH₂CH₂CH₂CH₂CH₂CH₂NCO<br>hexamethylene diisocyanate<br>7 moles | CH₂=CHS CH₂CH₂OH<br>vinyl hydroxyethylsulfide<br>6 moles |
| 19. | N,N,N¹,N¹-tetrakis (2-hydroxypropyl) ethylenediamine<br>Wyandotte Quadrol<br>2 mole | 2,4-tolylene diisocyanate<br>7 mole | H—N—(CH₂—CHCH=CH₂)₂<br>di(3-benzylallyl) amine<br>6 moles |
| 20. | Phosphorous based Polyol<br>Pluracol® 208 Polyol<br>Wyandotte Chem. Corp.<br>2 mole | methylene bis(4-phenyl isocyanate)<br>3 mole | CH₂—OCH₂CH=CH₂<br>HOCH₂—C—CH₂CH₃<br>CH₂—OCH₂CH=CH₂<br>1,1,1-trimethylolpropanediallyl ether<br>2 more |
| 21. | HO—(CH₂CH₂CH₂CH₂O)ₙ—H<br>Polymeg from Quaker Oats Co.<br>2 mole | methylene bis(4-cyclohexyl isocyanate)<br>3 mole | HO—(CH₂—CH)ₙ—CH=CH₂<br>omega-undecyleneyl alcohol |

| Example No. | Component [A] | Component [B] | Component [X] |
|---|---|---|---|
| 22. | HO–C(=O)–CF$_2$CF$_2$–C(=O)–OH<br>tetrafluorosuccinic acid<br>10 mole | diphenylsilanediol (Ph$_2$Si(OH)$_2$)<br>9 mole | HO–CH$_2$CH$_2$–N(CH$_3$)–CH=CH$_2$<br>N-Methyl-N-vinyl ethanolamine<br>2 mole |
| 23. | 2-hydroxy-3-mercapto cyclohexanol (1,2-cyclohexanediol with S)<br>1,2-cyclohexanediol<br>5 mole | 1,5-naphthalene diisocyanate<br>6 mole | HO–CH$_2$–C(=CH$_2$)–(2-pyridyl)<br>2-(2-pyridyl)-allyl alcohol |

CURING PROCESS

Example 24

0.01 mole of the allyl-terminated liquid Prepolymer A was charged to a 2 oz. glass bottle along with a stoichiometric amount to react with the allyl groups, i.e. 0.0066 moles, of trimethylolpropane tris($\beta$-mercaptopropionate) having a molecular weight of 398. The liquid reactants were stirred together and heated for 1/2 hour at 140°C. Thereafter the reactants were left under ambient conditions of room temperature and pressure. After 2½ days the liquid reactants became viscous and at the end of a 2 week period, a solid, self-supporting, cured, odorless, elastomeric polythioether product resulted.

EXAMPLE 25

0.005 moles of the allyl-terminated liquid Prepolymer E was charged to a 2 oz. glass jar along with a stoichiometric amount of a polythiol to react with the allyl groups in Prepolymer E, 0.0036 moles of trimethylolpropane tris ($\beta$-mercaptopropionate). The liquid reactants were stirred together briefly at room temperature and allowed to stand under ambient conditions. After eight hours a solid, odorless, self-supporting cured elastomeric polythioether polymer resulted.

EXAMPLE 26

643 g. (0.32 moles) of a commercially available poly(propylene ether) glycol sold under the tradename "Pluracol P 2010" by Wyandotte Chemical Co. was degassed at room temperature for 1 hour and then charged to a resin kettle maintained under a nitrogen atmosphere and equipped with a condenser, stirrer, thermometer and gas inlet and outlet. 111.4 g. (0.64 moles) of a 80–20% isomer mixture of tolylene-2,4-diisocyanate and tolylene-2,6-diisocyanate respectively sold under the tradename "Mondur TD 80" was added to the kettle. After 45 minutes, the temperature was raised to 120°C and the reaction was continued for 50 minutes. A sample was removed and titrated for NCO resulting in 33.54 mg NCO/g. 62.7 g. of diallyl amine was added at 105°C and the reaction was continued for 10 minutes. A sample was titrated resulting in an NCO content of 1.20 milligrams NCO/g. A vacuum was applied to the kettle for 1 hour at 90°C followed by cooling under nitrogen. The resulting product had a molecular weight of about 2,540–2,580 and an ene functionality of 4.

10 g. of the thus formed polymer was charged to a 2 oz. glass jar along with 2 g. of pentaerythritol tetrakis ($\beta$-mercaptopropionate and 0.5 g. acetophenone. The liquid reactants were briefly stirred together and placed out-doors under ambient conditions. Within 15 minutes a solid, odorless, elastomeric cured polythioether product was obtained.

EXAMPLE 27

40 g. of Prepolymer A and 10 g. of a filler sold commercially under the tradename "Hi Sil 233" by Columbia Southern Chemical Corp. were charged under nitrogen to a 200 ml. round bottom 3 necked flask maintained under a nitrogen atmosphere and mixed thoroughly. The flask was heated by a water bath to 60°C under full vacuum for 2 hours. The flask was then allowed to cool under vacuum. 4 g. of pentaerythritol tetrakis ($\beta$-mercaptopropionate) was charged to the flask under nitrogen and the reaction was stirred continuously. After 6½ days under nitrogen, no cure was noted. The reaction was then exposed to oxygen from the atmosphere and a solid, cured, odorless elastomeric product resulted within 45 minutes.

EXAMPLE 28

30 g. of Prepolymer A and 2.9 g. of "Q43" pentaerythritol tetrakis ($\beta$-mercaptopropionate) by Carlisle Chemical Co.) were admixed and cured by the presence of 1.5 g. of benzoyl peroxide and 0.3 g. dimethyl aniline as a peroxide activator. The curing time was 3 minutes and the solid, odorless, elastomeric cured polythioether product was found to have a Shore A hardness of 23.

EXAMPLE 29

20 g. of an aliphatic diisocyanate-derived urethane polyene of Example 21 was mixed in an aluminum dish with 2.2 g. of pentaerythritol tetrakis (β-mercaptopropionate) commercially available from Carlisle Chemical Co. under the tradename "Q43" and 0.5 g. of acetophenone. The mixture was irradiated for 3 minutes by ultraviolet light from a Sylvania Sun lamp. The sample cured to a tack-free solid which had a color of less than 1 on the Gardner Scale. After exposure to ultraviolet radiation in a Fadeometer for 47.2 hours, the color increased to a value of 4 on the Gardner Scale.

A similar polymer prepared from Polymeg glycol of molecular weight of about 1,000 by Quaker Oats Co., tolyene-2,4-diisocyanate and allyl alcohol, cured with pentaerythritol tetrakis (β-mercaptopropionate) and acetophenone by irradiation with ultraviolet light also had a Gardner color of less than 1. However, after 47.2 hours in the Fadeometer the Gardner color rose to 13.

The molecular weight of the polyenes of the present invention may be measured by various conventional methods. including solution viscosity, osmotic pressure and gel permeation chromatography. Additionally, the molecular weight may be calculated from the known molecular weight of the reactants.

The viscosity of the polyenes and polythiols may be measured on a Brookfield Viscometer at 30° of 70°C in accord with the instructions therefor.

The components to be cured may be prepared as either single-packaged or multi-packaged liquid polymer systems which may be cured to solid polythioether elastomers without liberating gaseous by-products which cause bubbles and voids in the vulcanizate. Thus, there is provided curable liquid polymer systems composed of polyenes and polythiols in which the components individually are storage stable and which are not sensitive to or deteriorated by traces of moisture or oxygen containing gas such as may be encountered during normal storage or handling procedures. Solid resinous or elastomeric products may be prepared from flowable liquids in a system in which the rate of curing may be inhibited or retarded by the use of chemical inhibitors, antioxidants, inert atmospheres and the like. The cured product may be characterized as in the thermally and oxidatively stable state since there is no reactive carbon-to-carbon unsaturation in the main backbone chain.

Solid cured polythioether polymer products have many and varied uses, examples of which include but are not limited to adhesives; caulks; sealants; coatings; impregnants for porous substrates; filleting compounds; molded articles and the like.

As used herein the term polyene and the term polyne refers to single or complex species of alkenes or alkynes having a multiplicity of terminal reactive carbon-to-carbon unsaturated functional groups per average molecule. For example, a diene is a polyene that has two reactive carbon-to-carbon double bonds per average molecule, while a diyne is a polyyne that contains in its structure two reactive carbon-to-carbon triple bonds per average molecule. Combinations of reactive double bonds and reactive triple bonds within the same molecule are also possible such as for monovinylacetylene which is a polyeneyne under this definition. For purpose of brevity all these classes of compounds are referred to hereafter as polyenes.

In defining the position of the reactive functional carbon-to-carbon unsaturation, the term terminal is intended to mean that functional unsaturation is at an end of the main chain in the molecule; whereas by near terminal is intended to mean that the functional unsaturation is not more than 10 carbon atoms and typically less than 8 carbon atoms from an end of the main chain in the molecule. The term pendant means that the reactive carbon-to-carbon unsaturation is located terminal or near-terminal in a branch of the main chain as contrasted to a position at or near the ends of the main chain. For purposes of brevity all of these positions are referred to herein generally as terminal unsaturation.

Functionality as used herein refers to the average number of ene or thiol groups per molecule in the polyene or polythiol, respectively. For example a triene is a polyene with an average of three reactive carbon-to-carbon unsaturated groups per molecule and thus has a functionality (f) of three. A dithiol is a polythiol with an average of two thiol groups per molecule and thus has a functionality (f) of two.

It is to be understood that the functionality of the polyene and the polythiol component is commonly expressed in whole numbers although in practice the actual functionality may be fractional. For example, a polyene component having a nominal functionality of 2 (from theoretical considerations alone) may in fact have an effective functionality of somewhat less than 2. In an attempted synthesis of a diene from a glycol in which the reaction proceeds to 100% of the theoretical value for complete reaction, the functionality (assuming 100% pure starting materials) would be 2.0. If however, the reaction were carried to only 90% of theory for complete reaction, about 10% of the molecules present would have only one ene functional group, and there may be a trace of material that would have no ene functional groups at all. Approximately 90% of the molecules, however, would have the desired diene structure and the product as a whole then would have an actual functionality of 1.9. Such a product is useful in the instant invention and is referred to herein as having a functionality of 2.

The term reactive unsaturated carbon-to-carbon groups means groups which will react under proper conditions as set forth herein with thiol groups to yield the thioether linkage

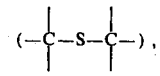

as contrasted to the term unreactive carbon-to-carbon unsaturation which means

groups found in aromatic nucleii (cyclic structures exemplified by benzene, pyridine, anthracene, and the like) which do not under the same conditions react with mols to give thioether linkages.

Highly water-sensitive groups are intended to include, for example, isocyanate, acyl halide such as acyl chloride, anhydride and the like which readily and rapidly react with water, alcohol, ammonia, amines and the like.

Odorless has been used herein to mean the substantial absence of the well-known offensive and sometimes obnoxious odors that are characteristic of hydrogen sulfide and the derivative family of compounds known as mercaptans.

The term non-yellowing means the substantial resistance to unsightly or uncontrollable discoloration during exposure to actinic radiation such as exposure to sunlight or to mechanical substitutes. Mechanical substitutes for sunlight include means such as a Fadometer having a source of ultraviolet radiation, or a Weatherometer which combines exposure to ultraviolet radiation with exposure to water.

It is understood that the foregoing detailed description is given merely by way of illustration and that many variations may be made therein without departing from the spirit of this invention.

carbon atoms and said cycloalkyl having from 3 to 8 carbon atoms; wherein [A] is free of reactive carbon-to-carbon unsaturation and formed of at least two repeating units selected from the group consisting of $+CH_2+_g$, $+C_2H_4O+_h$, $+C_3H_6O+_h$, and $+C_4H_8O+_h$, $g$ is an integer from 1 to 9 and $h$ is an integer from 1 to 200; said compound having a molecular weight in the range of 300 to 20,000 and a viscosity in the range from essentially 0 to 20 million centipoises at 70°C; and wherein $R_7$ is a member of the group consisting of hydrogen, phenyl, cycloalkyl, alkyl, and $CH_2=CH-$, wherein said alkyl has from 1 to 9 carbon atoms, said cycloalkyl has from 3 to 8 carbon atoms, and n is at least 1.

2. The polyene compound of claim 1 having the formula:

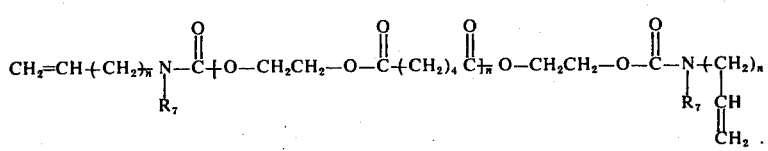

What is claimed is:

1. A polyene compound which comprises the formula:

3. The polyene compound of claim 1 having the formula:

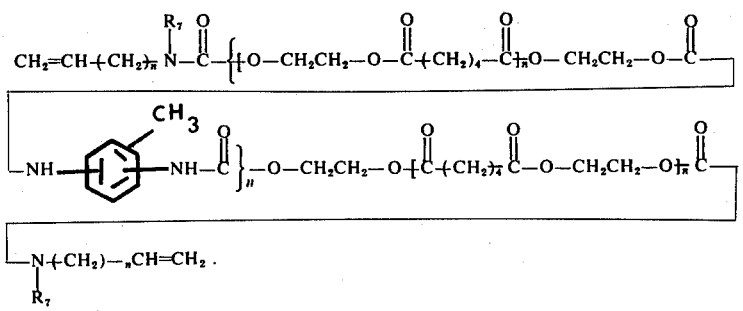

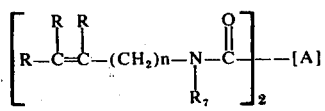

4. The polyene composition of claim 1 having the formula:

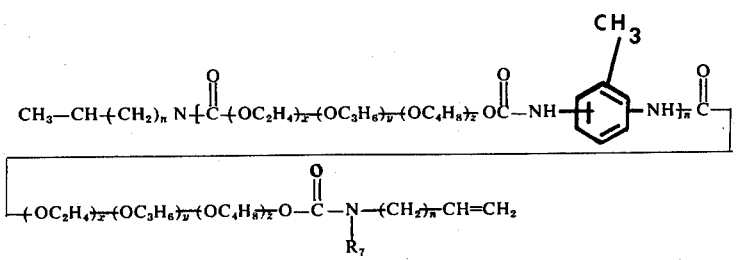

wherein R is a radical selected from the group consisting of hydrogen, fluorine, chlorine, phenyl, benzyl, alkyl, and cycloalkyl; said alkyl having from 1 to 9 wherein the sum of $x + y + z$ in each chain segment is at least 1.

5. A polyene compound having the formula:

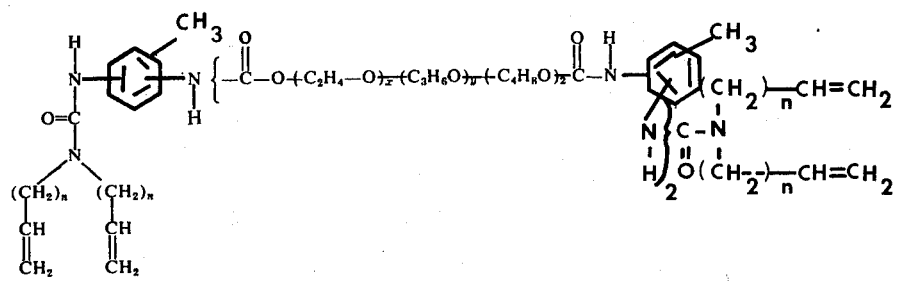

wherein the sum of $x + y + z$ is at least 1; $n$ is at least 1; and P is at least 2; said compound having a molecular weight in the range of 300 to 20,000 and a viscosity in the range from essentially 0 to 20 million centipoises at 70° C.

* * * * *